United States Patent [19]

Rosenstreich et al.

[11] 3,932,609

[45] Jan. 13, 1976

[54] ANTIPERSPIRANT COMPOSITION

[75] Inventors: Joseph Rosenstreich, Merrick; Joseph Gubernick, Port Washington; Frank Garone, Kings Park, all of N.Y.

[73] Assignee: Estee Lauder Inc., New York, N.Y.

[22] Filed: Mar. 29, 1974

[21] Appl. No.: 456,515

[52] U.S. Cl. ................................. 424/68
[51] Int. Cl.² ............................... A61K 7/38
[58] Field of Search ............... 424/68, 47, 66, 65

[56] References Cited

UNITED STATES PATENTS

| | | | |
|---|---|---|---|
| 2,571,030 | 10/1951 | Govett et al. | 424/68 X |
| 2,814,584 | 11/1957 | Daley | 424/66 |
| 3,018,223 | 1/1962 | Siegal | 424/68 |
| 3,107,252 | 10/1963 | Lubowe | 424/68 X |
| 3,198,708 | 8/1965 | Henkin et al. | 424/68 |
| 3,632,596 | 1/1972 | Mecca | 424/68 X |
| 3,634,480 | 1/1972 | Sheffield | 424/47 X |

FOREIGN PATENTS OR APPLICATIONS

| | | | |
|---|---|---|---|
| 1,335,358 | 10/1973 | United Kingdom | 424/47 |

OTHER PUBLICATIONS

Sagarin Cosmetics Science and Technology, 1957, pp. 1053 and 1054.

*Primary Examiner*—Dale R. Ore
*Attorney, Agent, or Firm*—Blum, Moscovitz, Friedman & Kaplan

[57] ABSTRACT

A stable antiperspirant liquid composition which is particularly suitable for use as an antiperspirant roll-on comprising an aluminum astringent material, a small but effective amount of a quaternary ammonium salt and fumed silica in an aqueous medium.

8 Claims, No Drawings

ANTIPERSPIRANT COMPOSITION

BACKGROUND OF THE INVENTION

The present invention relates to a stable antiperspirant liquid composition which is particularly suitable for use as an antiperspirant roll-on comprising an aluminum astringent material, a small but effective amount of a quaternary ammonium salt and dispersible fumed silica in an aqueous medium.

Antiperspirant liquids which are packaged in roll-on containers are known in the art. Such packaged antiperspirants include a suitable roll-on applicator above the liquid level which is rotatably mounted in the container discharge orifice whereby the antiperspirant liquid discharged onto the applicator may be selectively applied to the desired area.

In general, these prior antiperspirant liquids have exhibited reduced levels of activity after prolonged storage, particularly at elevated temperatures. The reduction in activity of such compositions has been attributed to a phase separation or constituent layering which occurs therein after prolonged storage, particularly at elevated temperatures.

Accordingly, there is an existent need for a stable antiperspirant liquid composition with a substantially uniform level of activity throughout the useful life thereof, even when stored for prolonged periods of time at elevated temperatures.

SUMMARY OF THE INVENTION

Generally speaking, in accordance with the invention, it has now been found that there may be prepared a stable antiperspirant liquid composition with a substantially uniform level of activity throughout the useful life thereof comprising an aluminum astringent material, a small but effective amount of a quaternary ammonium salt and fumed silica in an aqueous medium. The composition possesses a number of desirable properties, particularly with respect to roll-on characteristics.

Accordingly, it is an object of this invention to provide a novel composition which exhibits effective antiperspirant characteristics.

Another object of the invention is to provide an antiperspirant lotion composition which is stable throughout the useful life thereof.

A further object of the invention is to provide an antiperspirant lotion composition which is active throughout the useful life thereof.

Yet another object of the invention is to provide an antiperspirant lotion composition which is particularly suitable for use in a roll-on applicator.

Another object of the invention is to provide an antiperspirant lotion composition which is stabilized by inclusion therein of a small but effective amount of a quaternary ammonium salt and a select amount of fumed silica.

Still other objects and advantages of the invention will, in part, be obvious and will, in part, be apparent from the specification.

The invention accordingly comprises a composition possessing the characteristics, properties, and the relation of constituents which will be exemplified in the composition hereinafter described, and the scope of the invention will be indicated in the claims.

DESCRIPTION OF THE PREFERRED EMBODIMENTS

The stable antiperspirant liquid of the invention is preferably formulated within proportions such that the form thereof is a lotion which is particularly suited for use in a roll-on applicator. The antiperspirant lotion comprises an aluminum astringent material, a small but effective amount of a quatarnary ammonium salt and a select amount of water dispersible fumed silica in an aqueous medium. The lotion is substantially uniform and homogeneous in the container therefor. The presence of a select amount of fumed silica and a small but effective amount of a quaternary ammonium salt in the liquid medium stabilizes the composition and upon application thereof to a select area, there is applied a substantially uniform coating.

The aluminum astringent material employed in the antiperspirant lotion composition preferably includes a major proportion of aluminum chlorohydrate and a minor proportion of a highly ionizable aluminum salt soluble in an aqueous solvent medium. A particularly preferred embodiment includes a minor amount of aluminum chlorohydroxy allantoinate, viz. from about 0.27 to about 0.75% by weight thereof.

The aluminum chlorohydrate is a known water-soluble antiperspirant ingredient and is employed in complete form. In general, the commercial aluminum chlorohydrate has an approximate atomic ratio of aluminum to chlorine of 2:1 and an empirical formula of $Al_2(OH)_5Cl$ in aqueous solution. It may be employed in granular or solution form. The term aluminum chlorhydrate includes herein other equivalent aluminum chlorhydroxy complexes and their salts. Such other materials include aluminum chlorhydroxy ethylate complex, sodium aluminum chlorhydroxy lactate, and the like. The proportion of aluminum chlorhydrate in the final composition is variable but, in general, it should be from about 12 to about 20% by weight dissolved in the solvent medium.

Suitable highly ionizable aluminum salts employed in minor proportion in the aluminum astringent material include, particularly, the aluminum salts of mineral acids, for instance, aluminum chloride and other halides, aluminum sulfate, and the like. Other aluminum salts are aluminum sulfamate, aluminum phosphate and aluminum phenolsulfamate. A small but effective amount of these salts, and preferably from about 1 to about 3% by weight of aluminum chloride, dissolved in the solvent medium, enhance the antiperspirant activity of the aluminum chlorohydrate.

The solvent medium is water and preferably deionized water to avoid introducing trace amounts of reactants into the lotion composition. The amount of water in the final composition is variable and as suffices is generally added to the make-up and up to about 65% by weight may be employed.

A buffering material, such as an amide compound, for example, urea, ethyl carbamate or acetamide is employed. Alternatively, an amino carboxy acid, such as glycine or alanine, or the like, may be employed for its known effects. Preferably, the buffering material comprises an admixture of urea and glycine and the admixture thereof is added to the lotion composition in sufficient amounts to bring the pH thereof to between about 3.20 to 3.50. Optimum results are obtained by adding from about 3 to about 15% by weight of urea and from about 2 to about 8% by weight of glycine.

The composition comprising the aluminum astringent material, buffering material and water is a homogeneous, single phase liquid product. Upon application from the container, it has been noted that the applied coating is tacky, tends to rewet and dries only after prolonged exposure to the ambience. Moreover, the antiperspirant activity of the composition tends to decrease after prolonged storage.

It has been found that the incorporation of a small but effective amount of a quaternary ammonium salt and a select amount of water dispersible fumed silica results in a lotion wherein the applied lotion is characterized by decreased tack, decreased rewetting and prompt drying. There is no apparent decrease in the antiperspirant activity of the lotion composition even after prolonged storage. Furthermore, there is insured maximum stability of the composition until the contents of the container are exhausted.

The fumed silica is water dispersible, preferably having a particle size of between about 0.007 and 0.050 microns, a density of 4.0 – 5.0 lbs./cu. ft. and a surface area of between about 50 and 400 m²/gm. One particularly suitable fumed silica material is CAB-O-SIL "MS-7" (tradename of Cabot Corporation) which is a fumed silica produced by the hydrolysis of silicon tetrachloride at 1100°C. The fumed silica material should be used in the antiperspirant lotion in quantities of the order of up to 15% by weight and preferably from about 5 to 12% by weight on the composition is employed. It may be incorporated in the composition by any suitable method such as by slow addition to the liquid with agitation of the aqueous mixture so as to form a substantially homogeneous dispersion.

It is a critical parameter of compositions within the scope of the invention that the concentration of fumed silica therein be at least 5% by weight. Less than 5% by weight thereof renders the composition unstable. More than 12.5% by weight of fumed silica provides a composition that is too viscous for roll-on application. Optimal results are obtained when the concentration of fumed silica is between about 0 to 11% by weight.

The quaternary ammonium salt should be employed in the composition in extremely small quantities of the order of up to about 1% by weight and preferably from about 0.1 to 0.8% by weight on the composition. At concentrations of the quaternary ammonium salt which are less than 0.1%, the composition is unstable. Therefore, it is critical that at least 0.1% thereof be employed therein. When more than 1% by weight of the quaternary ammonium salt is employed, the composition is too viscous for roll-on application.

While various suitable water soluble quaternary ammonium salts may be employed in the composition, a particularly preferred group are the octyl aryloxy ethoxy ethyl dimethyl benzyl ammonium chlorides wherein the aryloxy group is phenoxy or cresoxy. The preferred component of this group is diisobutyl phenoxy ethoxy ethyl dimethyl benzyl ammonium chloride monohydrates with the formula:

It has been found that the stability and the viscosity of the composition are functionally related to the relative amounts of the quaternary ammonium salt and fumed silica present therein. While the mechanism is unknown, it is believed that the quaternary ammonium salt and fumed silica form a complex which stabilizes the composition and provides the desired viscosity. When either the quaternary ammonium salt or fumed silica is omitted, the composition is unstable and non-viscous. In particular, it appears that the effect of the quaternary ammonium salt on stability and viscosity of the composition is surprisingly disproportionate to the amount thereof employed in the composition as particularly shown in Example II set forth below. It is also found that at a fixed concentration of the quaternary ammonium salt, a small increase in the fumed silica concentration has a surprising effect upon the viscosity of the composition, as particularly shown in Example III set forth below.

The viscosity of the composition is variable but, in general, it should be from about 500 to about 2,225 cps., and preferably 700 to 1100 cps. at ambient temperature. The antiperspirant lotions having a viscosity of 700 to 1100 cps. are particularly preferred. These particularly preferred antiperspirant lotions are further characterized by a specific gravity of about 1.100 to about 1.400 at ambient temperature and a volatiles content of about 58.5% + 1.0%.

Various adjuvant materials may be incorporated in the composition in suitable amounts. There is preferably employed a known preservative material, such as sorbic acid. While any of the conventional preservatives may be employed, the preservative selected must function on the acidic side. The amount of preservative added to the composition is variable but, in general, it should be from about 0.1 to about 0.4% by weight. Minor amounts of other materials such as perfume, deodorants, antiseptic, germicidal or bacteriostatic substances, may be added also if desired.

The following formulations are illustrative of the nature of the present invention and it is to be understood that the invention is not limited thereto. All percentages are by weight unless otherwise indicated.

EXAMPLE I

| Ingredient | Percent |
| --- | --- |
| Aluminum Chlorhydrate (50% aqueous solution) | 33.00 |
| Aluminum Chloride (50% aqueous solution) | 4.00 |
| Diisobutyl phenoxy ethoxy ethyl dimethyl benzyl ammonium chloride monohydrate (50% aqueous solution) | 0.60 |
| Urea | 8.00 |
| Glycine | 4.00 |
| Aluminum Chlorhydroxy Allantoinate | 0.50 |
| Sorbic acid | 0.40 |
| Fumed Silica | 10.50 |
| Deionized Water | Balance |

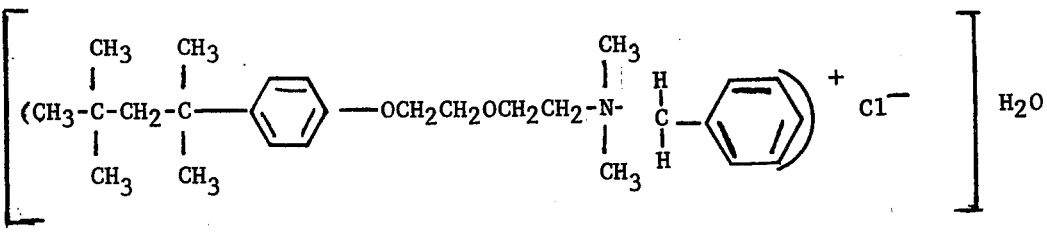

The aluminum chlorhydrate in the form of an aqueous solution, the aluminum chloride in the form of an aqueous solution, the quaternary ammonium salt and the water are added with stirring to form a homogeneous liquid. The urea, glycine, aluminum chlorhydroxy allantoinate and sorbic acid are added thereto with stirring and the temperature of the admixture is raised to about 50° to about 55°C with constant agitation. At a temperature of about 50°C, the fumed silica is slowly added to the admixture with constant stirring to form a fine dispersion and the temperature thereof is maintained at about 50° to about 55°C. The final product is then added to a polyethylene squeeze bottle provided with a roll-on applicator in the outlet orifice thereof which may be closed with a bottle cap. Upon squeezing of the plastic bottle or suitably orienting the plastic bottle for underarm usage, this composition as applied from the roll-on applicator produces a uniform antiperspirant coating.

the surprising effect of the quaternary ammonium salt on the properties of the composition.

EXAMPLE III

| Ingredient | Percent: Sample 1 | Sample 2 | Sample 3 | Sample 4 |
|---|---|---|---|---|
| Aluminum Chlorhydrate (50% aqueous solution) | 33.00 | 33.00 | 33.00 | 33.00 |
| Aluminum Chloride (50% aqueous solution) | 4.00 | 4.00 | 4.00 | 4.00 |
| Diisobutyl phenoxy ethoxy ethyl dimethyl benzyl ammonium chloride monohydrate (50% aqueous solution) | 0.60 | 0.60 | 0.60 | 0.60 |
| Urea | 8.00 | 8.00 | 8.00 | 8.00 |
| Glycine | 4.00 | 4.00 | 4.00 | 4.00 |
| Aluminum Chlorhydroxy Allantoinate | 0.50 | 0.50 | 0.50 | 0.50 |
| Sorbic Acid | 0.40 | 0.40 | 0.40 | 0.40 |
| Fumed Silica | 2.50 | 5.00 | 10.50 | 12.50 |
| Deionized Water | 47.00 | 44.50 | 39.00 | 37.00 |
| Viscosity: Brookfield Viscometer, LVT Model Spindle No. 3 at 30 rpm. for 1 minute - 48 hours after manufacturing | 50 cps. | 500 cps. | 1,025 cps. | 2,225 cps. |
| Stability: Overnight at 50°C | Unstable | Stable | Stable | Stable |
| Room Temperature | Unstable | Stable | Stable | Stable |

The above formulations were prepared as in Example I and resulted in products having the illustrated characteristics. In all the samples, the amount of quaternary ammonium salt was held constant while the concentration of fumed silica was varied from 2.5 to 12.50% by weight. Sample 1 which contained 2.50% by weight of fumed silica was unstable and had a viscosity of 50 cps. At the other end of the spectrum, sample 4 contained 12.50% by weight of fumed silica and was stable, but that formulation was characterized by a viscosity of 2,225 cps. Samples 3 and 4 were compared and it was observed that the increase of 2.00% by weight of fumed silica in sample 4 resulted in a more than twofold increase in the viscosity. That increase is surprising in view of comparisons that may be made among samples 1–3.

EXAMPLE II

| Ingredient | Percent: Sample 1 | Sample 2 | Sample 3 |
|---|---|---|---|
| Aluminum Chlorhydrate (50% aqueous solution) | 33.00 | 33.00 | 33.00 |
| Aluminum Chloride (50% aqueous solution) | 4.00 | 4.00 | 4.00 |
| Diisobutyl phenoxy ethoxy ethyl dimethyl benzyl ammonium chloride monohydrate (50% aqueous solution) | — | 0.60 | 1.00 |
| Urea | 8.00 | 8.00 | 8.00 |
| Glycine | 4.00 | 4.00 | 4.00 |
| Aluminum Chlorhydroxy Allantoinate | 0.50 | 0.50 | 0.50 |
| Sorbic Acid | 0.40 | 0.40 | 0.40 |
| Fumed Silica | 10.50 | 10.50 | 10.50 |
| Deionized Water | 39.60 | 39.00 | 38.60 |
| Viscosity: Brookfield Viscometer, LVT Model Spindle No. 3 at 30 rpm. for 1 minute- 48 hours after manufacturing | 0 cps. | 1,025 cps. | 3,160 cps. |
| Stability: Overnight at 50°C | Unstable | Stable | Stable |
| Room temperature | Unstable | Stable | Stable |

The above formulations were prepared as in Example I and resulted in products having the stability and viscosity characteristics set forth in Samples 1–3. The fumed silica concentration was constant and the quaternary ammonium salt concentration was varied. Sample 1 contained no quaternary ammonium salt and was characterized as unstable having a viscosity of 0 cps. In Sample 3, the amount of quaternary ammonium salt employed was 1.00% by weight and while the composition was stable, it was characterized by a viscosity of 3,160 cps. Sample 2 was formulated in the manner set forth in Example I and the resulting product was suitably stable and viscous. The comparative samples show Although the present invention has been described with reference to particular embodiments and examples, it will be apparent to those skilled in the art that variations and modifications of this invention can be made and that equivalents can be substituted therefor without departing from the principles and true spirit of the invention.

It is also to be understood that the following claims are intended to cover all of the generic and specific features of the invention herein described, and all statements of the scope of the invention which, as a matter of language, might be said to fall therebetween.

What is claimed is:

1. A stable antiperspirant lotion composition which is particularly suitable for use in a roll-on applicator comprising from about 12 to about 20% by weight of aluminum chlorhydrate, from about 1 to about 3% by weight of aluminum chloride, from about 5 about 12% by weight of fumed silica, from about 0.1 to about 1% by weight of a quaternary ammonium salt selected from the group consisting of octyl phenoxy ethoxy ethyl dimethyl benzyl ammonium chloride and octyl cresoxy ethoxy ethyl dimethyl benzyl ammonium chloride, a buffer material in an amount sufficient to adjust the pH of said composition to between about 3.20 and 3.50 and the remainder of the composition being water, said lotion composition being characterized by a viscosity of from about 500 to about 2,225 cps at ambient temperature.

2. The lotion composition of claim 1 wherein said composition is characterized by a viscosity of about 700 to 1100 cps at ambient temperature, said lotion composition including a volatiles content of about 58.5% ± 1.0%.

3. The antiperspirant lotion composition of claim 1 including from about 0.27 to about 0.75% by weight of aluminum chlorhydroxy allantoinate.

4. The antiperspirant lotion composition of claim 1 wherein said buffering material comprises from about 3 to about 15% by weight of urea and from about 2 to about 8% by weight of glycine.

5. The antiperspirant lotion composition of claim 1 said fumed silica having a particle size of between about 0.007 and 0.050 microns, a density of 4.0 to about 5.0 lbs./cm. ft. and a surface area of between about 50 and 400 $cm^2/gm$.

6. The antiperspirant lotion composition of claim 1 wherein said quaternary ammonium salt is diisobutyl phenoxy ethoxy ethyl dimethyl benzyl ammonium chloride monohydrate, said lotion composition including from about 0.1 to 0.8% by weight thereof.

7. The antiperspirant lotion composition of claim 1 including from about 0.1 to about 0.4% by weight of an acid active preservative.

8. The antiperspirant lotion composition of claim 7 wherein said preservative is sorbic acid.

* * * * *